(12) United States Patent
Rossney et al.

(10) Patent No.: US 10,299,847 B2
(45) Date of Patent: May 28, 2019

(54) SYSTEMS AND METHODS FOR INTRAMEDULLARY NAIL IMPLANTATION

(71) Applicant: GLOBUS MEDICAL, INC., Audubon, PA (US)

(72) Inventors: Mark Rossney, Downingtown, PA (US); David J. Rowe, Parkesburg, PA (US); David R. Jansen, Glenmoore, PA (US); David Laird, Brandamore, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 0 days.

(21) Appl. No.: 15/272,850

(22) Filed: Sep. 22, 2016

(65) Prior Publication Data
US 2018/0078299 A1    Mar. 22, 2018

(51) Int. Cl.
*A61B 17/72* (2006.01)
*A61B 17/88* (2006.01)
*A61B 17/92* (2006.01)
*A61B 17/17* (2006.01)
(Continued)

(52) U.S. Cl.
CPC ........ *A61B 17/921* (2013.01); *A61B 17/1725* (2013.01); *A61B 17/72* (2013.01); *A61B 17/725* (2013.01); *A61B 17/7233* (2013.01); *A61B 17/7275* (2013.01); *A61B 17/7283* (2013.01); *A61B 17/744* (2013.01); *A61B 17/8872* (2013.01); *A61B 17/1742* (2013.01); *A61B 2017/90* (2013.01)

(58) Field of Classification Search
CPC ... A61B 17/921; A61B 17/72; A61B 17/1725; A61B 17/744; A61B 17/8897; A61B 17/1703; A61B 17/1721; A61B 17/175; A61B 2017/0092; A61B 2017/90; A61B 2017/00469; A61B 2019/5466
USPC ........................ 606/62, 64, 96–99, 104, 86 R
See application file for complete search history.

(56) References Cited

U.S. PATENT DOCUMENTS

| 4,667,664 | A | 5/1987 | Taylor et al. |
| 4,952,213 | A | 8/1990 | Bowman et al. |
| 5,034,013 | A | 7/1991 | Kyle et al. |

(Continued)

FOREIGN PATENT DOCUMENTS

| CN | 201524132 U | 7/2010 |
| DE | 3722852 A1 | 1/1989 |

(Continued)

*Primary Examiner* — Pedro Philogene

(57) ABSTRACT

Intramedullary nails, systems, and methods. The intramedullary nail may include a generally elongate body extending from a first, distal end to a second, proximal end. The distal end may include one or more openings configured to receive one or more bone anchors that extend transversely through the distal end intramedullary nail, and thereby configured to secure the distal end of the nail. The proximal end may also include one or more openings configured to receive one or more bone anchors that extend transversely through the proximal end of the intramedullary nail, and thereby configured to secure the proximal end of the nail. In some embodiments, the proximal end may further include a cross-locking feature, which includes a second bone anchor that interlocks with a first bone anchor, for example, for enhanced bone purchase and bony fixation.

18 Claims, 15 Drawing Sheets

(51) Int. Cl.
*A61B 17/74* (2006.01)
*A61B 17/90* (2006.01)

(56) References Cited

U.S. PATENT DOCUMENTS

| | | | |
|---|---|---|---|
| 5,167,663 A | 12/1992 | Brumfield | |
| 5,167,666 A | 12/1992 | Mattbeck et al. | |
| 5,312,406 A | 5/1994 | Brumfield | |
| 5,334,192 A * | 8/1994 | Behrens | A61B 17/1721 |
| | | | 606/102 |
| 5,433,720 A | 7/1995 | Faccioli et al. | |
| 5,549,610 A | 8/1996 | Russell et al. | |
| 5,613,971 A * | 3/1997 | Lower | A61B 17/1714 |
| | | | 606/102 |
| 5,728,128 A | 3/1998 | Crickenberger et al. | |
| 6,120,504 A | 9/2000 | Brumback et al. | |
| 7,131,974 B2 * | 11/2006 | Keyer | A61B 17/1622 |
| | | | 606/96 |
| 7,169,149 B1 * | 1/2007 | Hajianpour | A61B 17/60 |
| | | | 606/54 |
| 7,476,225 B2 | 1/2009 | Cole | |
| 7,686,808 B2 | 3/2010 | Orbay et al. | |
| 7,780,667 B2 | 8/2010 | Watanabe et al. | |
| 7,799,030 B2 | 9/2010 | Watanabe et al. | |
| 7,914,532 B2 | 3/2011 | Shaver et al. | |
| 7,927,336 B2 | 4/2011 | Rasmussen | |
| 8,062,304 B2 * | 11/2011 | Blain | A61B 17/025 |
| | | | 606/86 A |
| 8,083,742 B2 | 12/2011 | Martin | |
| 8,241,286 B2 * | 8/2012 | Metzinger | A61B 17/1703 |
| | | | 606/104 |
| 8,328,805 B2 | 12/2012 | Cole | |
| 8,360,970 B2 | 1/2013 | Mangiardi | |
| 8,449,544 B2 | 5/2013 | Grusin | |
| 8,518,040 B2 | 8/2013 | Schlienger et al. | |
| 8,591,513 B2 | 11/2013 | Overes et al. | |
| 8,715,283 B2 | 5/2014 | Brumfield et al. | |
| 8,790,343 B2 | 7/2014 | McClellan et al. | |
| 8,834,469 B2 | 9/2014 | Watanabe et al. | |
| 8,932,301 B2 | 1/2015 | Metzinger et al. | |
| 8,961,518 B2 | 2/2015 | Taylor et al. | |
| 9,101,432 B2 | 8/2015 | Limouze et al. | |
| 9,138,278 B2 | 9/2015 | Van Osten, III | |
| 9,155,582 B2 | 10/2015 | Felder et al. | |
| 9,166,582 B2 * | 10/2015 | Yang | G06F 3/044 |
| 9,173,664 B2 * | 11/2015 | Metzinger | A61B 17/1721 |
| 2002/0029041 A1 | 3/2002 | Hover et al. | |
| 2006/0111716 A1 | 5/2006 | Schlienger et al. | |
| 2013/0190570 A1 | 7/2013 | Hirsch et al. | |
| 2013/0282016 A1 | 10/2013 | Volpi et al. | |
| 2013/0317502 A1 | 11/2013 | Overes | |
| 2013/0325076 A1 | 12/2013 | Palmer et al. | |
| 2014/0243838 A1 | 8/2014 | Feibel et al. | |
| 2014/0276828 A1 | 9/2014 | Howling et al. | |
| 2014/0309648 A1 | 10/2014 | Matityahu | |
| 2015/0038967 A1 | 2/2015 | Khong et al. | |
| 2015/0265323 A1 | 9/2015 | Sems et al. | |
| 2016/0089189 A1 | 3/2016 | Buscaglia et al. | |

FOREIGN PATENT DOCUMENTS

| | | |
|---|---|---|
| DE | 4240277 A1 | 6/1993 |
| DE | 4445692 A1 | 5/1996 |
| EP | 2606836 A1 | 6/2013 |
| WO | 9415556 A1 | 7/1994 |
| WO | 2013092402 A1 | 6/2013 |

* cited by examiner

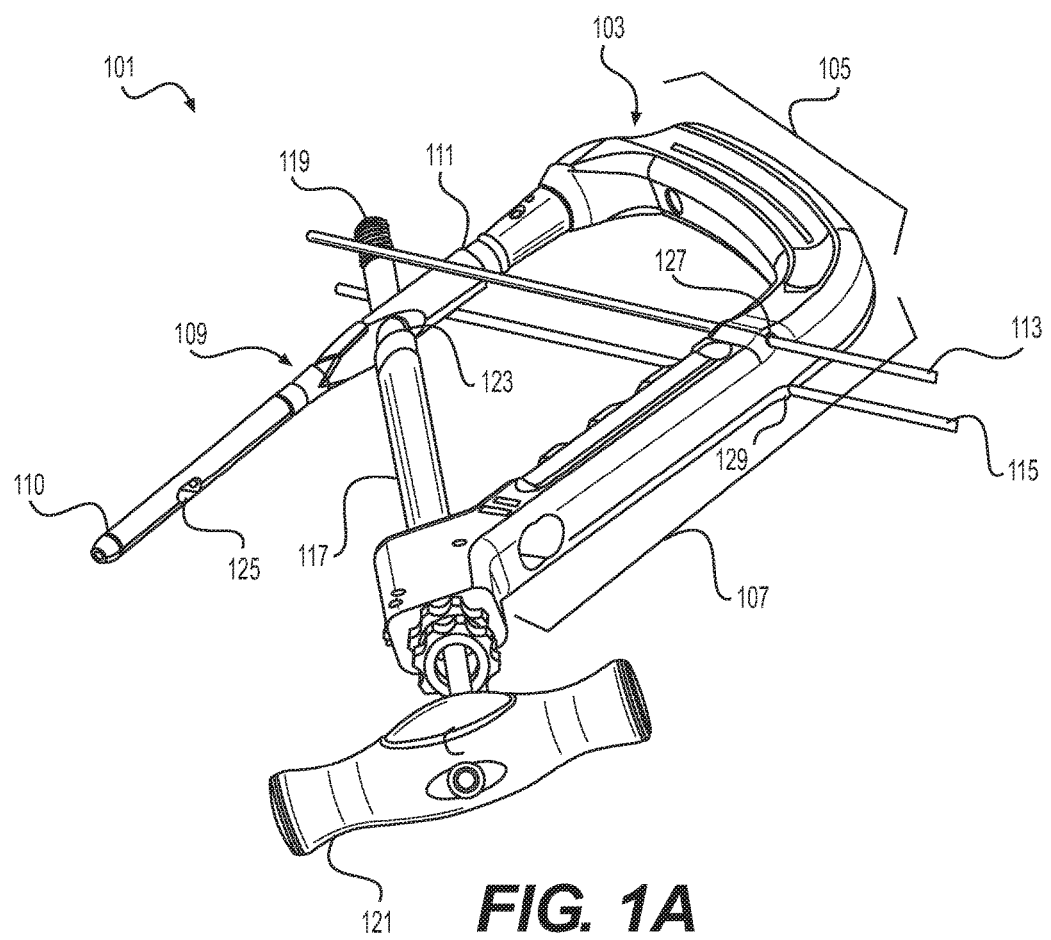

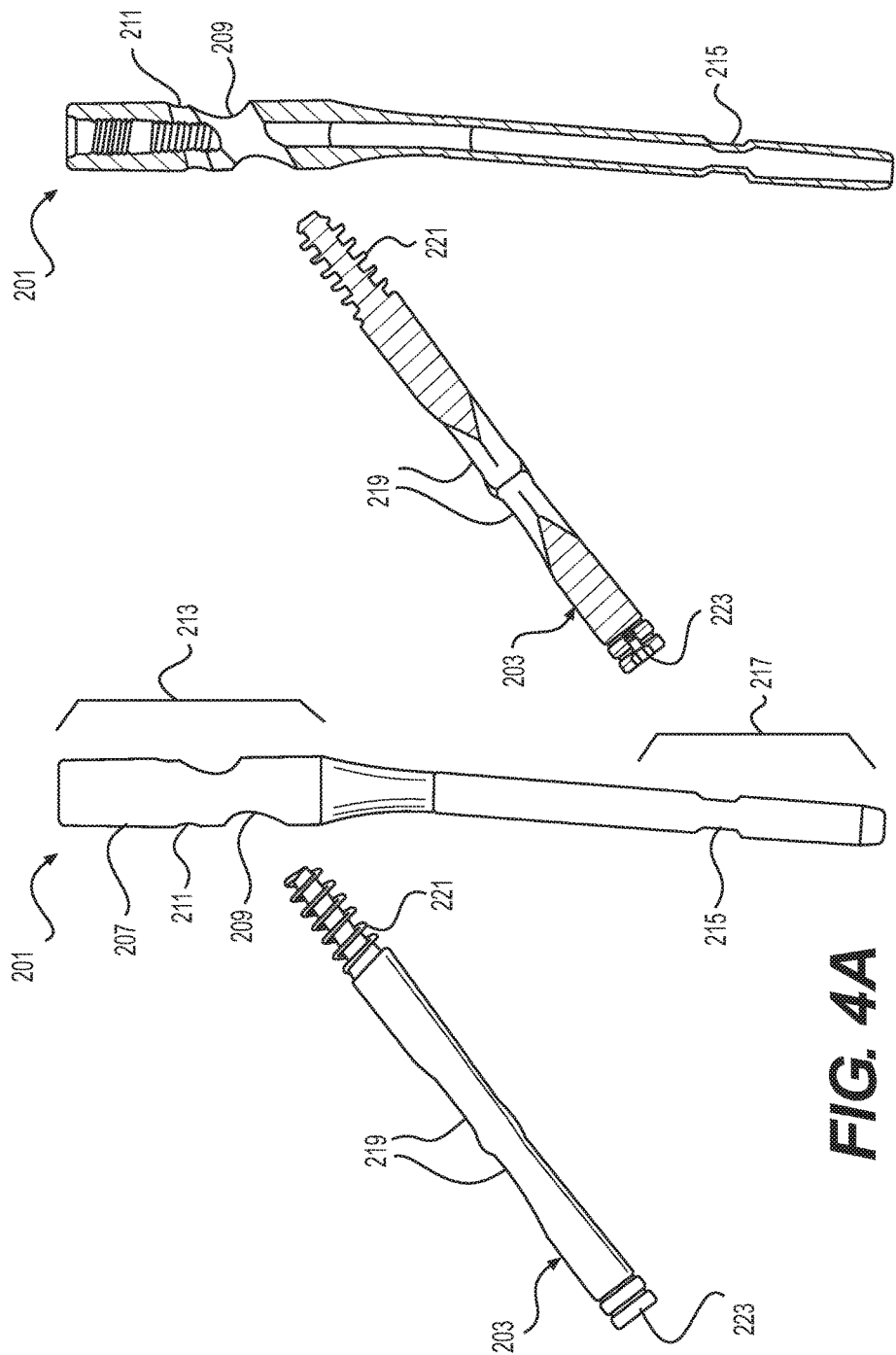

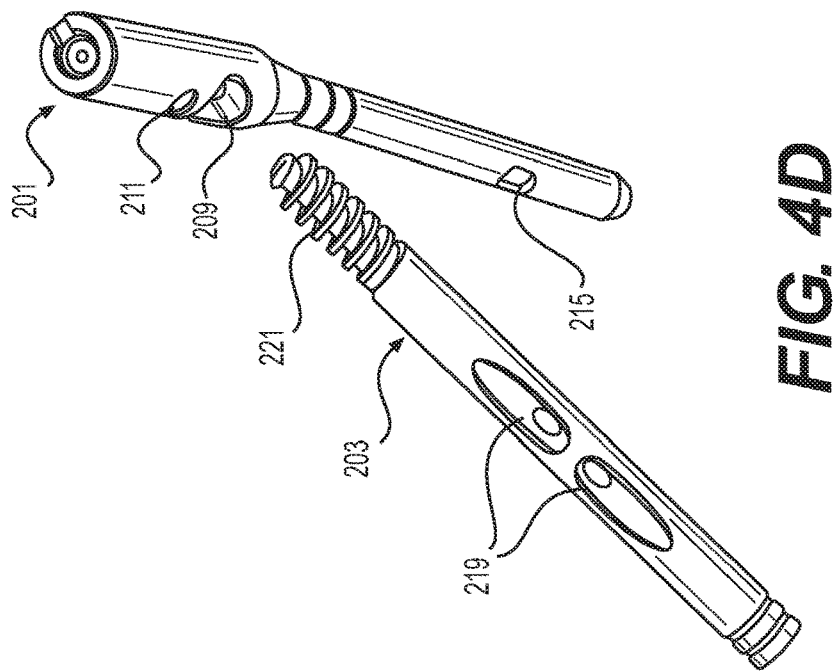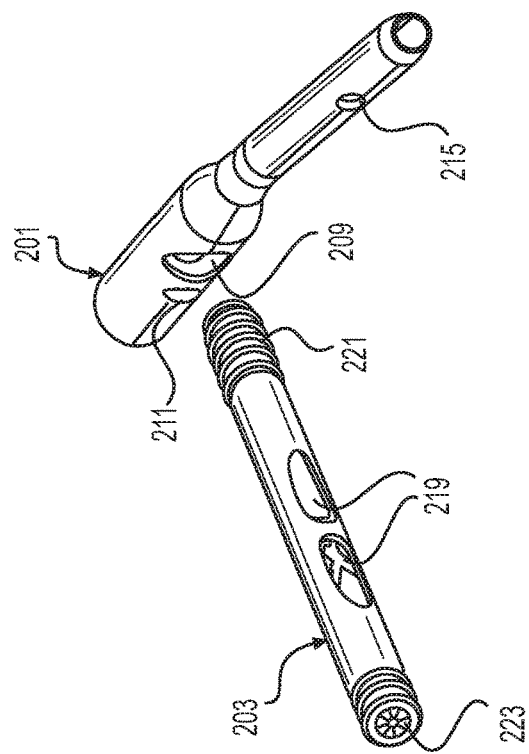

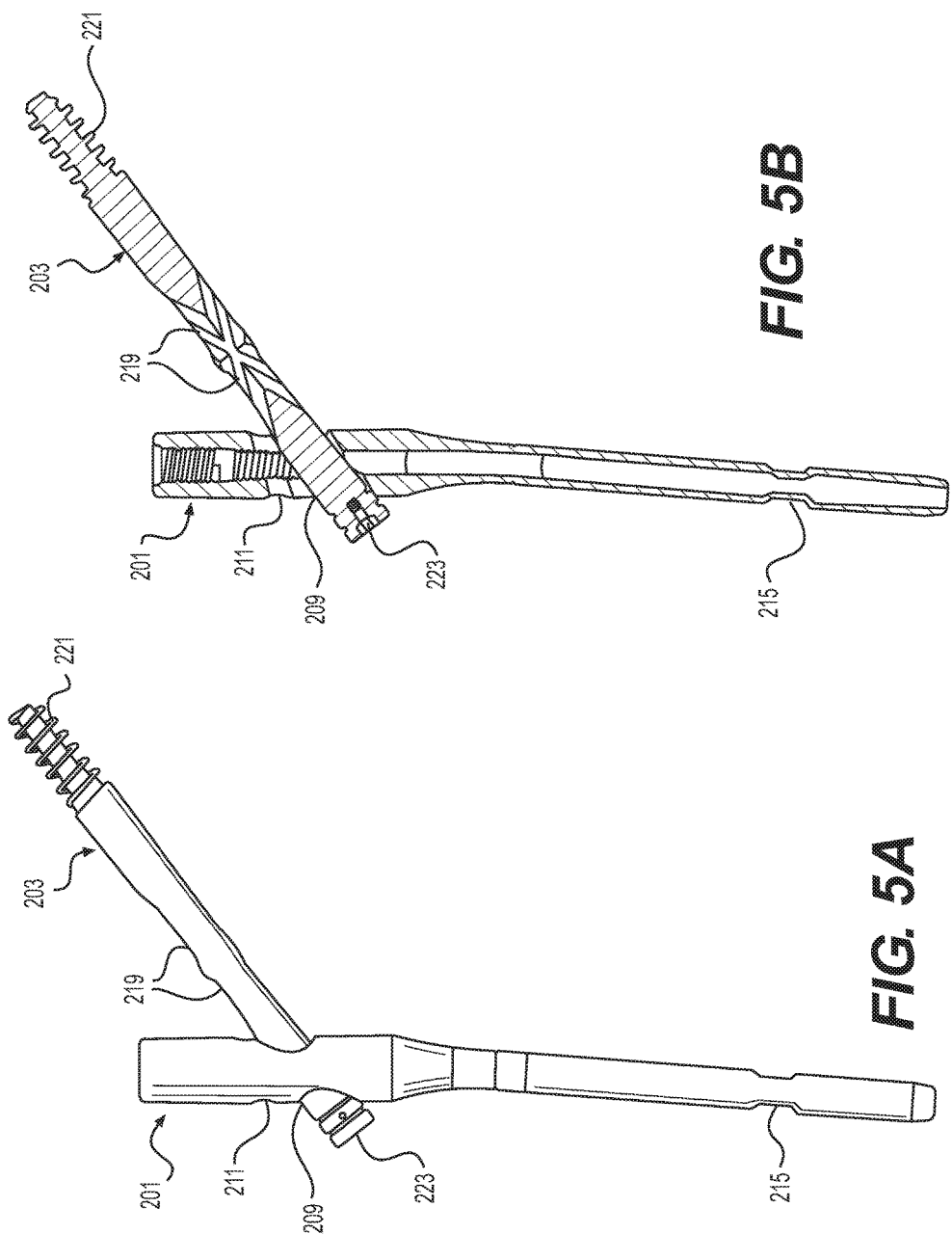

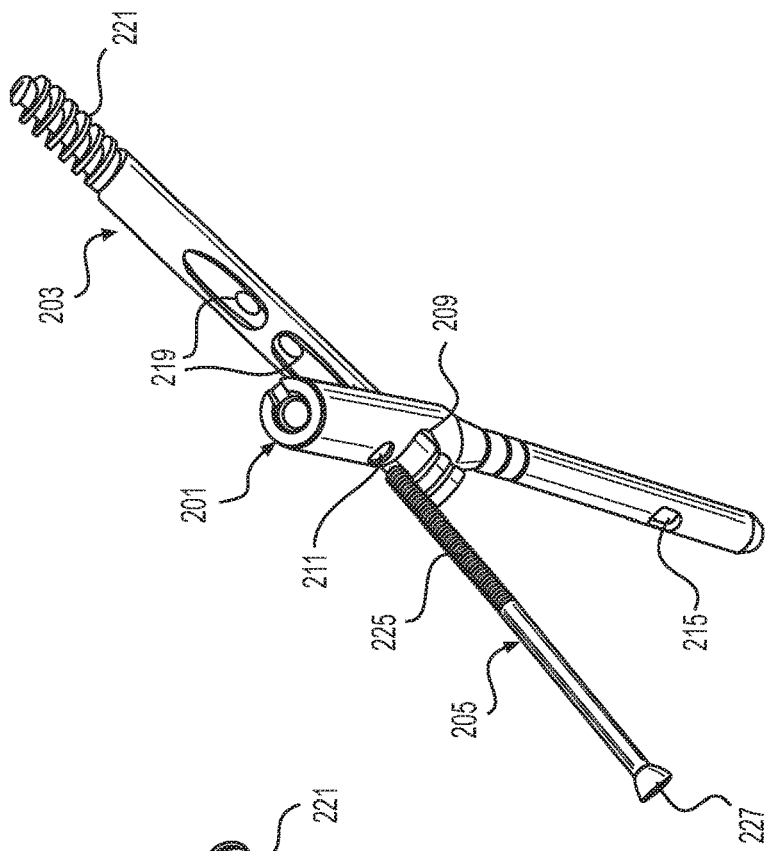
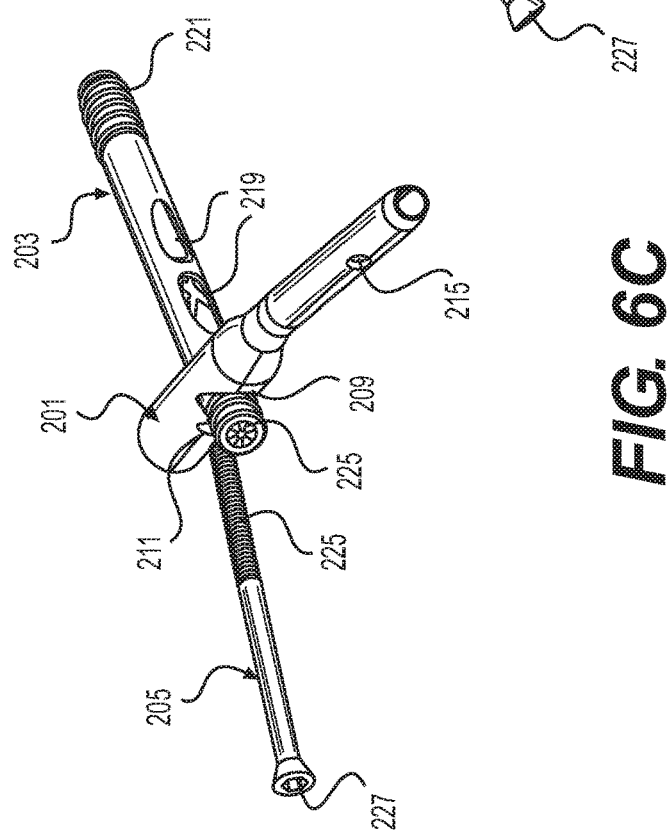
FIG. 6D
FIG. 6C

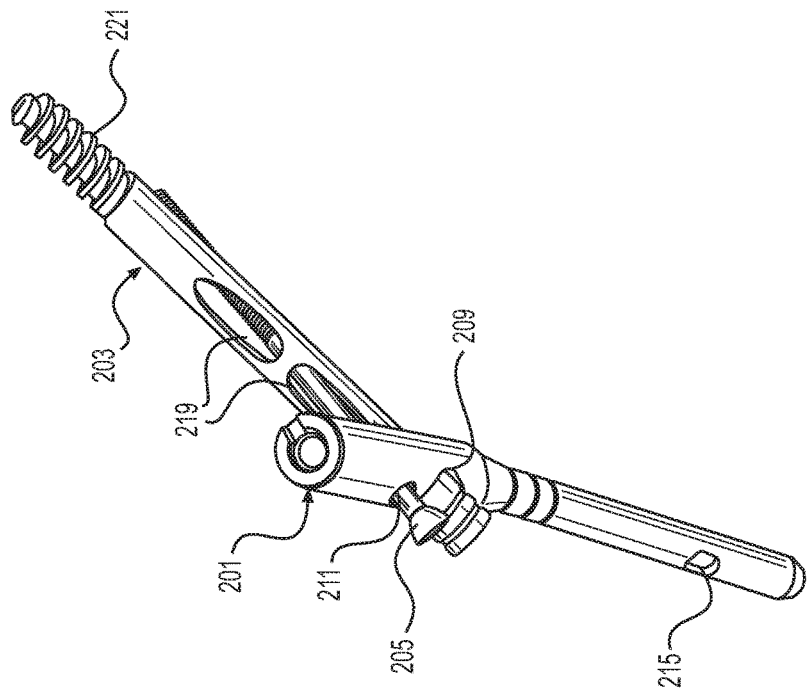
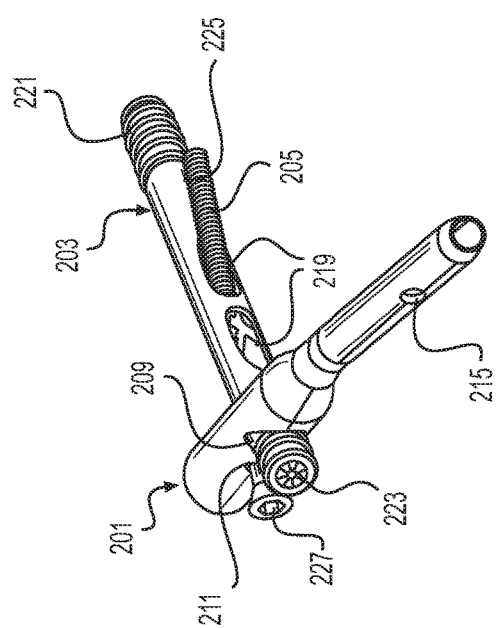
FIG. 7D
FIG. 7C

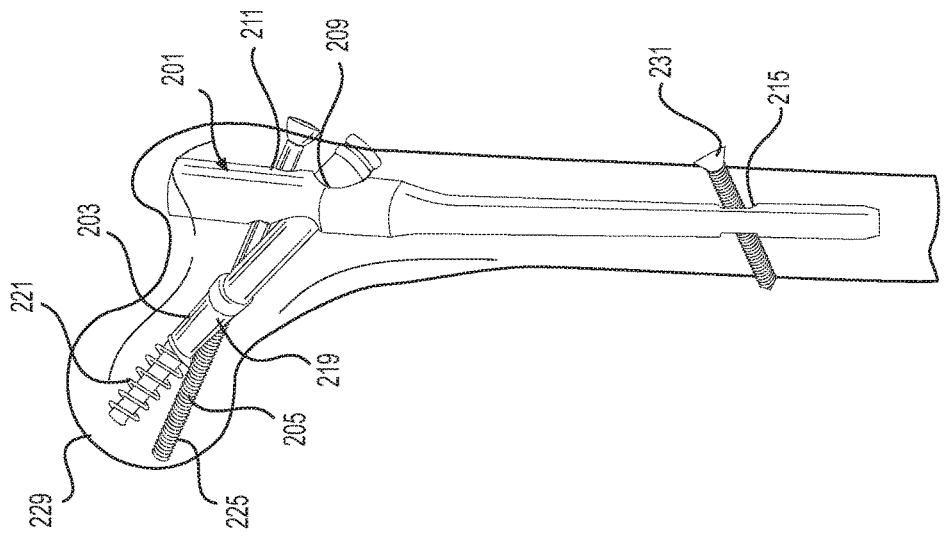
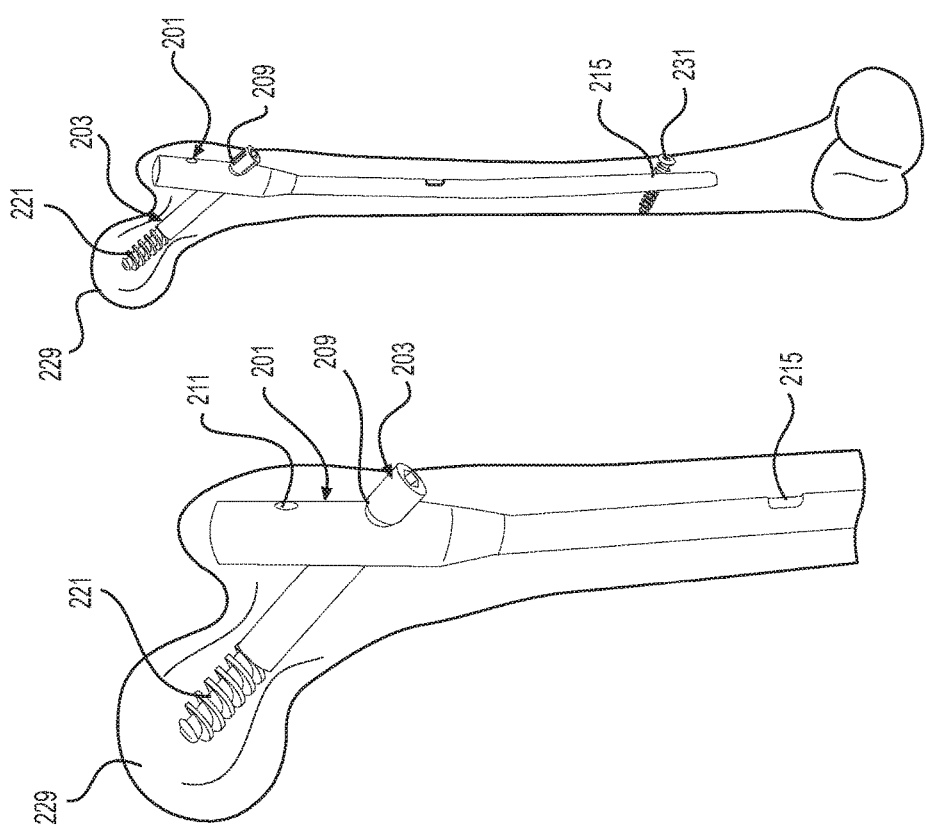

SYSTEMS AND METHODS FOR INTRAMEDULLARY NAIL IMPLANTATION

TECHNICAL FIELD

The present technology is generally related to intramedullary nail implantation for treatment of bone fractures. In particular, several embodiments are directed to systems and methods for implanting an intramedullary nail for immobilizing bone fractures.

BACKGROUND

The significant long bones of the extremities are the humerus, radius and ulna of the upper extremity and the femur and tibia of the lower extremity. Following an injury to the long bone, and in particular, injuries resulting in one or more fractures of the long bone, one or more fixation devices may be used to immobilize the fracture fragments and stabilize the long bone. Bone fractures can be treated with screws or other fixation devices inserted into or through the bone to stabilize it once the fractured portions have been brought into proper alignment. Femoral neck fixation, for example, can be used to treat hip fractures by inserting an intramedullary nail into the medullary cavity of the fractured femur followed by insertion of a fixation screw into the femoral neck/head at an angle relative to the intramedullary nail. Similarly, other long bone fractures can be treated by inserting an intramedullary nail into the intramedullary canal of the bone and providing the appropriate proximal and/or distal fixation. Traditional intramedullary devices may suffer from a number of disadvantages, however. For example, they may be susceptible to implant failure and difficulty in alignment of the fixation screw with respect to the intramedullary nail. Accordingly, there is a need for improved systems and methods for intramedullary nail implantation.

SUMMARY

Intramedullary nails, systems, insertion tools, and method of treatment are provided. The intramedullary nails may be suitable for implanting within a medullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although generally described with reference to the femur, it will be appreciated that the intramedullary nail and system may be adapted for use with any long bone.

According to one aspect, an intramedullary nail is provided. The intramedullary nail may comprise a generally elongate body extending from a first, distal end to a second, proximal end. The distal end may include one or more openings configured to receive one or more bone anchors or fasteners that extend transversely through the distal end intramedullary nail, and thereby configured to secure the distal end of the nail. The proximal end may also include one or more openings configured to receive one or more bone anchors or fasteners that extend transversely through the proximal end of the intramedullary nail, and thereby configured to secure the proximal end of the nail.

In one aspect, a system for inserting an intramedullary nail into a bone is provided. The system includes an intramedullary nail with an opening or aperture formed therein. An insertion tool includes can temporarily engage with an end of the intramedullary nail during implantation, and release from the nail once the procedure is complete. A receiving feature for a guide sheath (e.g., a hole, recess, etc.) is disposed in the handle portion and can receive a guide sheath therethrough. The receiving feature defines an axis such that, when the intramedullary nail is coupled to the coupling portion, a guide sheath inserted through the receiving feature substantially aligns with the aperture in the intramedullary nail. A first retention member is disposed in the insertion tool adjacent to the guide sheath receiving feature. The first retention member can interact with a second retention member on the guide sheath to form a ratchet-like mechanism that restrict movement of the guide sheath with respect to the receiving feature. A retention release mechanism can be located on a lower portion (e.g., a bottom surface) of the insertion tool. A guide wire receptacle (e.g., a hole, recess, etc.) can receives a guide wire therethrough and is positioned such that, when the intramedullary nail is coupled to the coupling portion, a guide wire inserted through the receiving feature runs along an axis adjacent to the side surface of the intramedullary nail.

In another aspect, a method for inserting an intramedullary nail into a patient is provided. The method includes inserting a nail into a medullary canal of a patient along a first axis. For insertion, the nail is coupled at its proximal end to an insertion tool. A guide wire is inserted through a guide wire hole in the insertion tool along a second axis such that the guide wire runs nearby or adjacent to a side surface of the nail. A screw or other bone fixation device is inserted through receptacle (e.g., a hole, recess, or other suitable structure) formed in the insertion tool such that the screw passes through an aperture formed in the nail.

In accordance with another aspect, an implant is provided. The implant includes an intramedullary nail that is elongated along a first axis. First and second openings or apertures are disposed in a proximal portion of the nail. The first aperture defines a second axis transverse to the first axis, and the second aperture defines a third axis transverse to the first axis. The third axis intersects with the second axis at a point spaced apart from the nail. In some embodiments, the first screw can be inserted through the first aperture along the second axis and a second screw can be inserted through the second aperture along the third axis. The second screw can be at least partially inserted through a slot in the first screw such that the two screws interlock. The second screw can be shorter than the first screw but long enough that at least a threaded distal tip extends beyond the slot in the first screw to provide some purchase in the bone.

Also provided are kits including intramedullary nails of varying shapes and sizes, bone anchors, fasteners, insertion tools, and components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 1A and 1B illustrate a system for implanting an intramedullary nail.

FIGS. 4A-4D illustrate various views of an intramedullary nail and a first fixation device.

FIGS. 5A-5D illustrate various views of the first fixation device inserted through the intramedullary nail.

FIGS. 6A-6D illustrate various views of a second fixation device and the intramedullary nail with the first fixation device inserted therein.

FIGS. 7A-7D illustrate various views of the second anchor inserted through the intramedullary nail and the first fixation device.

FIGS. 8A-8C illustrate steps of implanting an intramedullary nail with interlocking fixation devices into a fractured femur.

DETAILED DESCRIPTION

Figure 1B:
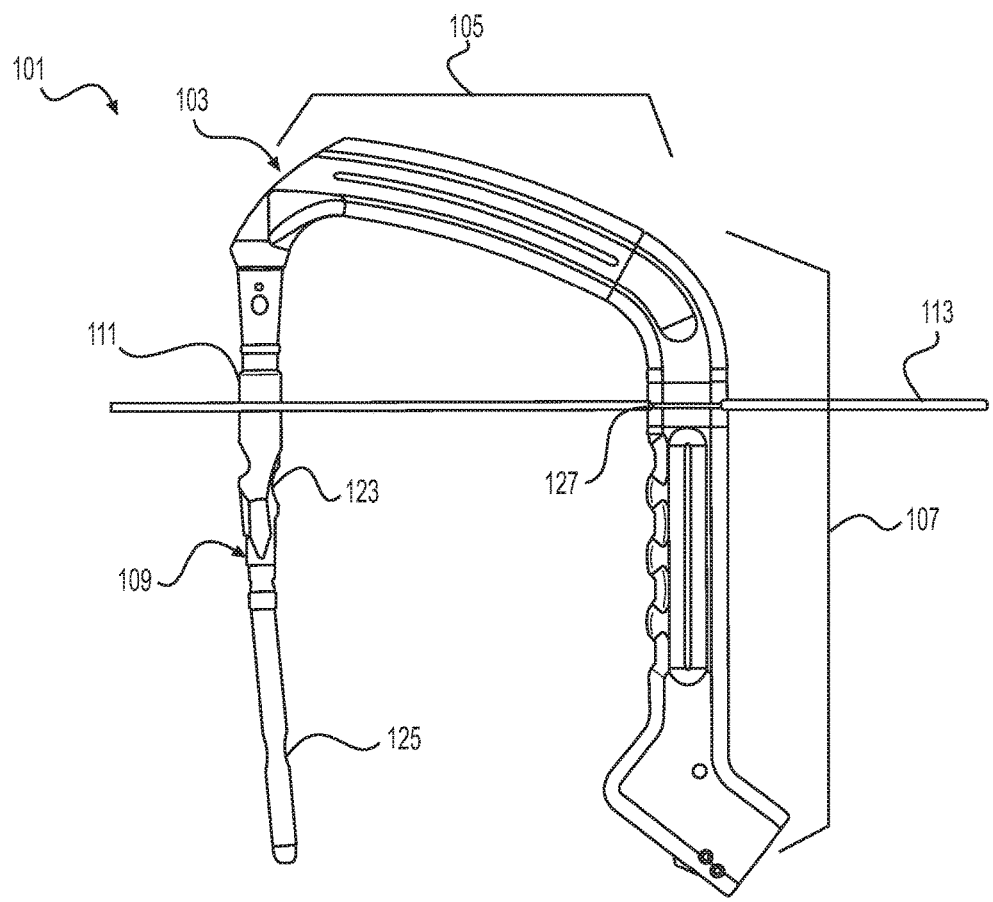

Intramedullary nails, systems, insertion tools, and method of treatment are provided. The intramedullary nails may be suitable for implantation within the intramedullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although further described with reference to hip fractures of the femur, it will be appreciated that the intramedullary nail and system may be adapted for use with any long bone.

In conventional hip fracture fixation techniques, there are four main failure modes: axial cutout, cephalad cutout, proximal fragment rotation, and nonunion. "Cutout" is the term for hip screw subsidence into the articular surface of the hip. Cutout can occur in either a cephalad (toward the head) or axial direction (along the axis of the hip screw). Axial cutout is the result of an implant with a small axial profile that provides little resistance to axial translation. Axial cutout can be addressed by the "controlled collapse" features on certain modern hip fracture nails; the hip screw is allowed to translate through the nail, even after the set screw is locked in place. Cephalad cutout is the radial translation of the nail which is the result of a narrow implant that "windshield wipers" through the weak cancellous bone in the hip. Proximal fragment rotation is the result of a circular profile hip screw that acts as a fulcrum to the proximal hip fragment. Fracture nonunion is the result of biologic or mechanical factors that are incompatible with the bone healing process. Biologic factors of the patient are not controllable by the implant. Mechanical factors are those that typically allow fixation that is too rigid or too flexible. Nonunion is usually the precursor to one of the other three failure modes. Occasionally, nonunion will cause the nail to break in fatigue before the bone fails.

The intramedullary nails and systems described herein may address one or more of these failure modes. In some embodiment, the intramedullary nail includes proximal and distal locking, for example, to prevent cutout. In other embodiments, the intramedullary nail may include proximal locking including two interlocking fixation devices (e.g., screws), for example, by providing converging and diverging purchase, along with bony fixation in the calcar of the femur, which is the strongest portion of the hip bone. Accordingly, the risk of failure due to cutout and/or rotation can be reduced.

Additionally, some intramedullary nail implantation systems fail to adequately address the problems of fragment rotation during implantation. Rotation occurs when fragments of the bone rotate about the axis of the screw during the implantation procedure. Conventional anti-rotation technologies require the use of additional instruments or are limited to a single wire placement. In some embodiments, an insertion tool is directly coupled to the intramedullary nail and additional instruments are not needed for the placement of an anti-rotation guide wire and allow the user to place one or more guide wires anterior and/or posterior to the nail. These guide wires can be positioned to prevent the distal fragments of the femoral head and neck from rotating about the axis of the anchor during the procedure.

Some systems may be susceptible to backout during the implantation procedure. Backout occurs when the guide sheath used to insert the screw through the intramedullary nail moves proximally away from the bone. Conventional systems either have no features to prevent backout or else provide backout prevention measures that obstruct the normal positioning of the hands during the procedure, resulting in the risk of releasing the guide sheaths and dropping them to the floor. Ratchets on the insertion tool may have the release button facing towards the grip portion on the insertion tool and may present the danger of the user's hand slipping and inadvertently pressing the button. Accidentally pressing the button could result in releasing the sheath and causing the sheath to fall on the floor. In some embodiments, a backout prevention system (e.g., a ratchet system) may be disposed on the lower end of the insertion tool, which allows a user to have a hand placed on the grip of the insertion tool without the risk of inadvertently pressing the ratchet release button.

Further specific details of several embodiments of the present technology are described below with reference to FIGS. 1A-8C. Although many of the embodiments are described below with respect to devices, systems, and methods for implantation of intramedullary nails, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Intramedullary Nail Implants and Systems

Figure 3A:
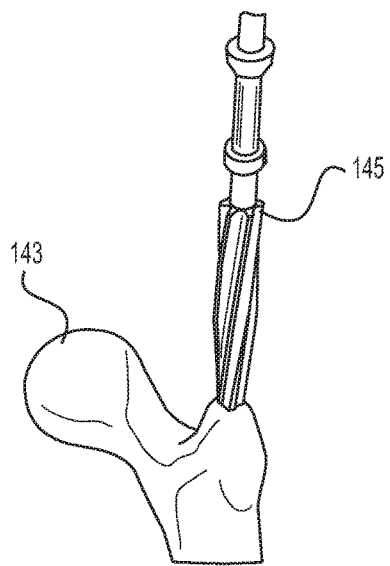
FIGS. 3A-3F illustrate steps of implanting an intramedullary nail into a fractured femur.
Figure 3B:
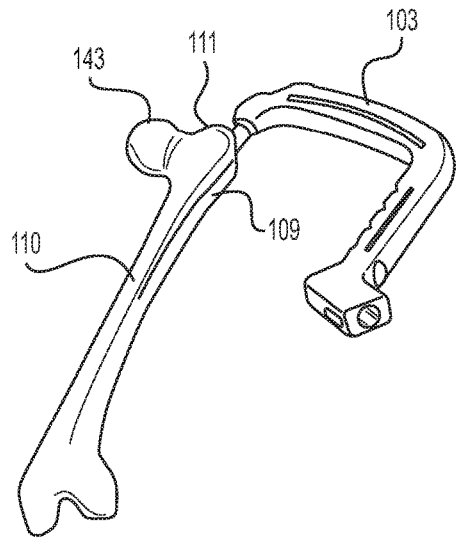
Figure 3C:
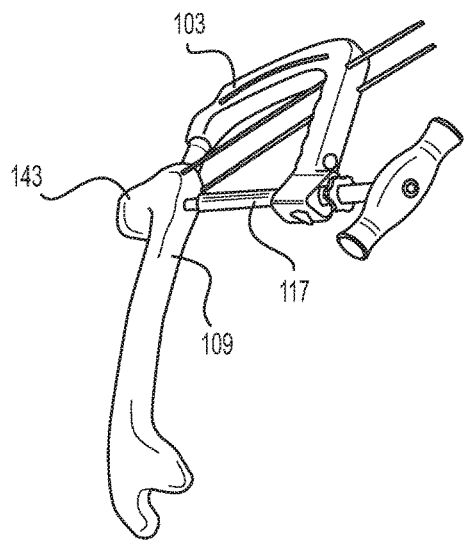
Figure 3D:
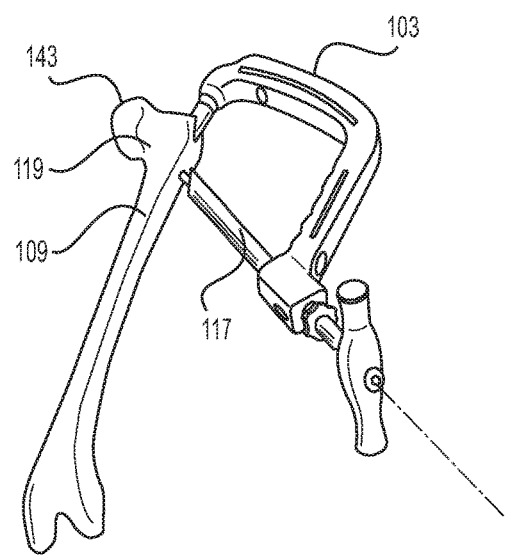
Figure 3E:
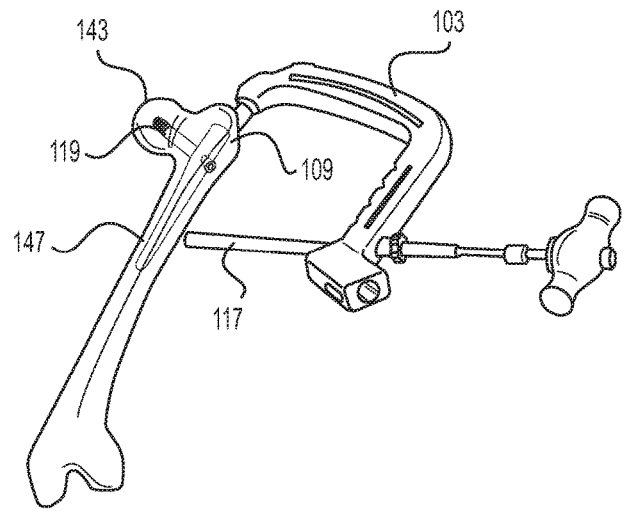
Figure 3F:
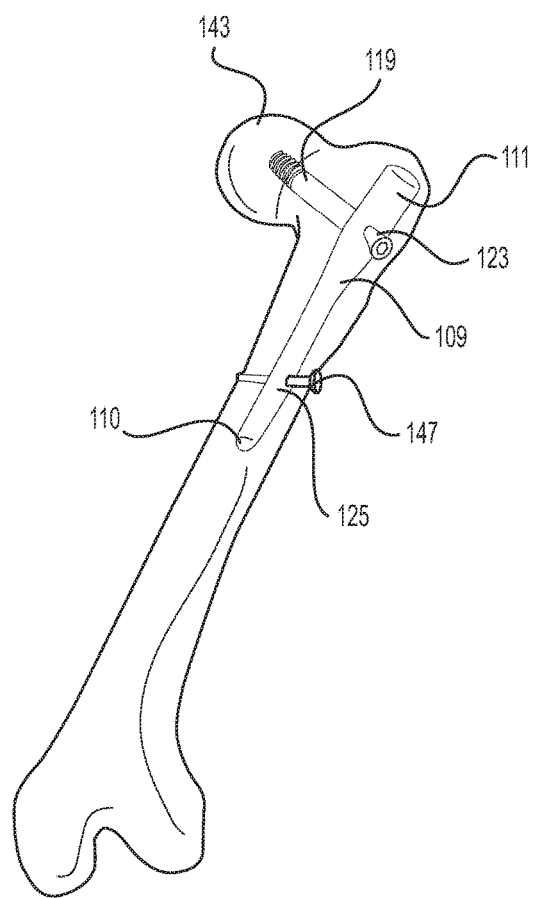
Figure 5D:
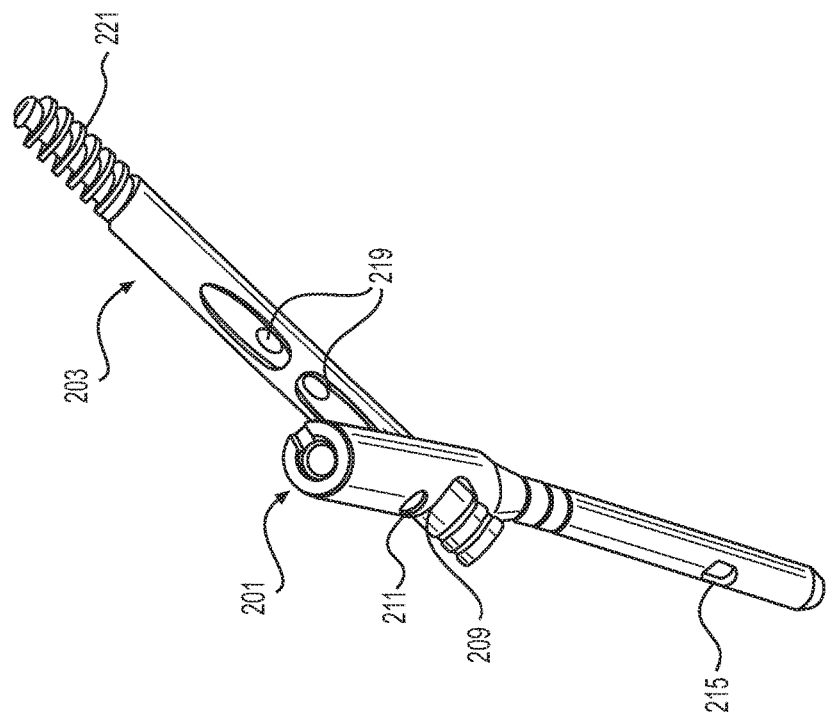
Figure 5C:
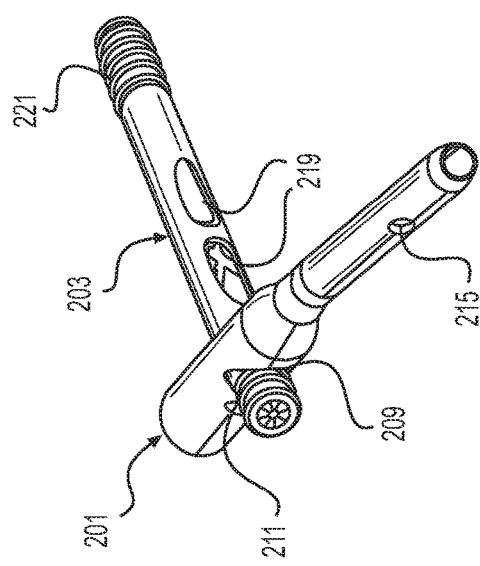
Figures 6A, 6B:
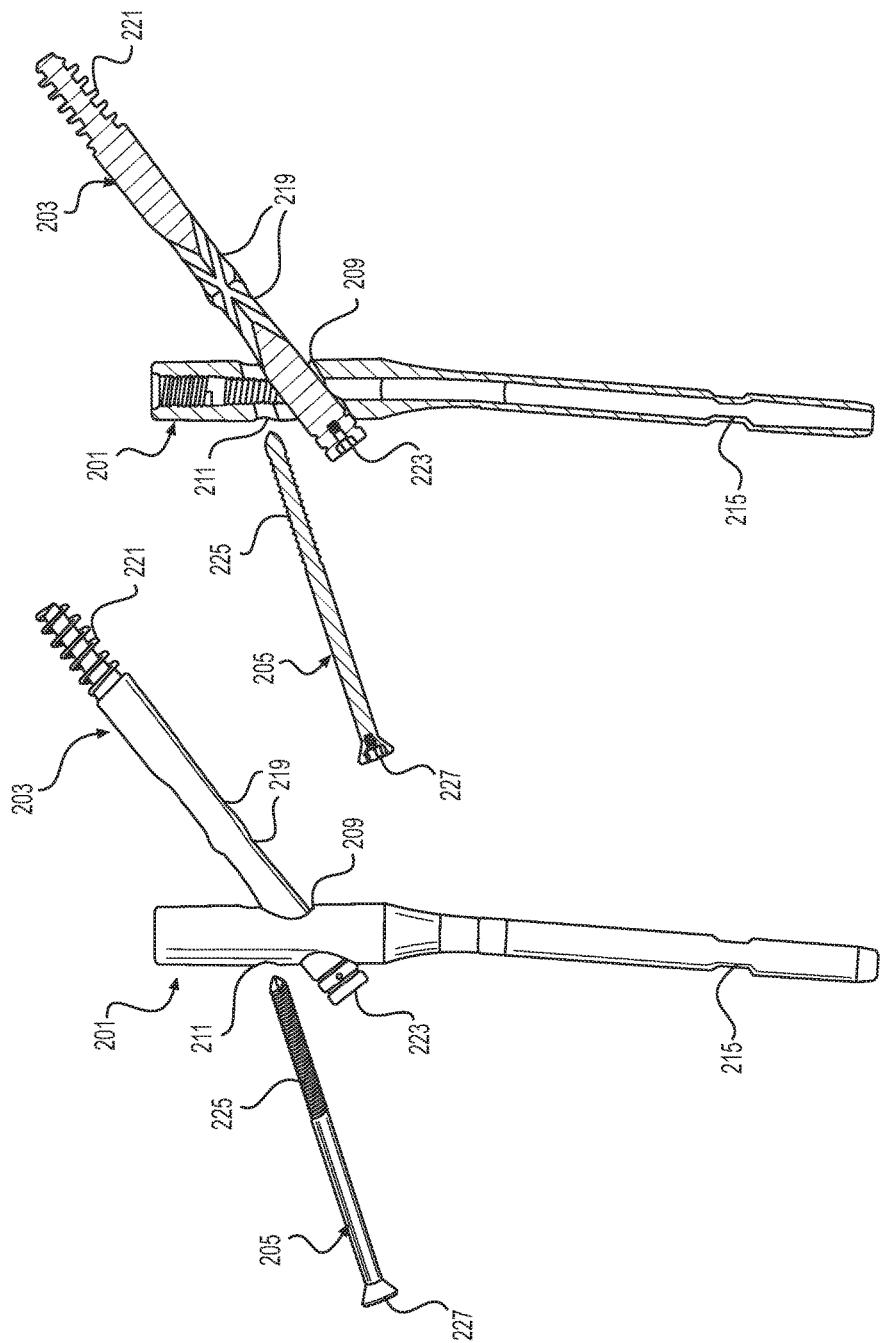

FIGS. 1A and 3F illustrate one example of an intramedullary nail 109, which may comprise a generally elongate body extending from a first, distal portion or end 110 to a second, proximal portion or end 111. The elongate body may be in the form of an elongate tubular rod configured to extend longitudinally within the intramedullary canal of a fractured bone. The elongate rod may be hollow or may be solid along its length. The elongate body may be substantially straight along a longitudinal axis of the nail 109 or may comprise one or more curves or bends to conform to the anatomical shape of the intramedullary canal. The cross-section of the nail 109, taken at a right angle to a central longitudinal axis of the intramedullary nail 109, may be circular, oval, elliptical, or of any other suitable cross-dimensional shape. The proximal portion 111 may have an enlarged diameter or head portion relative to the distal portion 110 of the nail 109. The enlarged head portion 111 may be sized and configured to be received in the greater trochanter region of the femur. The intramedullary nail 109 may be configured to be positioned in the proximal end of the femur for cephalomedullary fixation. It is envisioned, however, that the intramedullary nail 109 may be configured to be positioned through other approaches and locations (e.g., distal end) depending on the bone (e.g., femur, tibia) and type of fracture.

The distal end 110 may include one or more openings 125 configured to receive one or more bone anchors, fasteners, or distal fixation devices 147 that extend transversely through the distal end 110 of the intramedullary nail 109, and are thereby configured to secure the distal end 110 of the nail 109 within the canal. The distal fixation devices 147 may include a bone screw or anchor configured for distal locking of the nail 109. The distal fixation device 147 may include traditional polyaxial or fixed angle locking bone screws and anchors known in the art.

The proximal end 111 may also include one or more openings 123 configured to receive one or more bone anchors or fasteners 119 that extend transversely through the proximal end 111 of the intramedullary nail 109, and are thereby configured to secure the proximal end 111 of the nail 109 within the canal. The proximal fixation devices 119 may include a bone screw or anchor configured for proximal locking of the nail 109. The fixation device 119 may be a calcar screw or anchor configured to be aimed at a calcar region of the proximal humerus, which may constitute the best quality bone in the region. The opening 123 and anchor 119 may be angled about 100-150°, 110-140°, or about 120-135° relative to the nail 119 to engage the calcar region of the bone. The calcar screw 119 may have an enlarged diameter relative to the distal screw 147. The proximal fixation device 119 may include traditional polyaxial or fixed angle calcar screws and anchors known in the art. The proximal end 111 may also include additional openings 123, for example, for one or more cross-locking devices (e.g., device 205 described in more detail below).

The intramedullary nail 109 and anchors 119, 147 may be comprised of any suitable biocompatible materials. The intramedullary nail 109 and anchors 119, 147 may be comprised of titanium, cobalt chrome, cobalt-chrome-molybdenum, stainless steel, tungsten carbide, carbon composite, plastic or polymer—such as polyetheretherketone (PEEK), polyethylene, ultra high molecular weight polyethylene (UHMWPE), resorbable polylactic acid (PLA), polyglycolic acid (PGA), combinations or alloys of such materials, or other appropriate biocompatible materials that have sufficient strength to secure and hold bone, while also having sufficient biocompatibility to be implanted into a body.

System for Intramedullary Nail Implantation

FIGS. 1A and 1B illustrate perspective and side views, respectively, of one embodiment of a system 101 for implanting an intramedullary nail 109. The system 101 includes an insertion tool 103 that has a coupling portion 105 and a handle portion 107. In some embodiments, the coupling portion 105 and the handle portion 107 can be separate parts that are removably joined together, while in other embodiments the coupling portion 105 and the handle portion 107 can be different regions of a single, integrally formed component. The coupling portion 105 releasably engages or couples to the proximal portion 111 of the nail 109. For example, the free end of the coupling portion 105 can be provided with a snap-fit design to temporarily retain a position of the intramedullary nail 109 prior to insertion of a fixation device 119 therethrough. However, those skilled in the art will understand that other coupling mechanisms may be employed.

The handle portion 107 may include one or more openings 127, 129 configured to receive one or more guide wires 113, 115. In one embodiment, the system 101 may include first and second guide wires 113, 115 as well as an optional guide sheath 117 through which the fixation device 119 may pass (e.g., the fixation device 119 can be inserted using the driver 121). As illustrated, the first and second guide wires 113, 115 may pass on opposing sides of both the nail 109 and the fixation device 119 (e.g. on posterior and anterior sides). Although the illustrated embodiment shows two guide wires, in other embodiments a single guide wire and corresponding guide wire hole may be used. In still other embodiments, three or more guide wires may be used. Additionally, the position and orientation of the guide wire holes can vary in different embodiments, for example being disposed more proximally or more distally along the insertion tool, etc.

As illustrated, the insertion tool 103 allows the user to place one or more guide wires 113, 115. In one embodiment, the guide wires 113, 155 are positioned both anterior and posterior to the nail 109. The guide wires 113, 115 may be positioned in this manner to prevent the distal fragments of the bone (e.g., distal fragments of the femoral head and neck) from rotating about the axis of the fixation device 119 when the fixation device 119 is advanced through the nail 109 and into the bone during the procedure. The handle portion 107 of the insertion tool 103 may include two guide wire receiving features such as holes 127, 129 on the opposing sides of the tool 103 that allow guide wires 113, 115 to pass through the respective holes. The guide wires 113, 115 are passed through the soft tissue and into the bone to help stabilize the insertion tool 103. In this configuration, the insertion tool 103 may not require any other instruments to guide the wires 113, 115 into the patient. The insertion tool 103 can achieve stability by resisting both rotational movement about the axis of the nail 109 as well as axial translation along the axis of the nail 109.

Figure 2A:
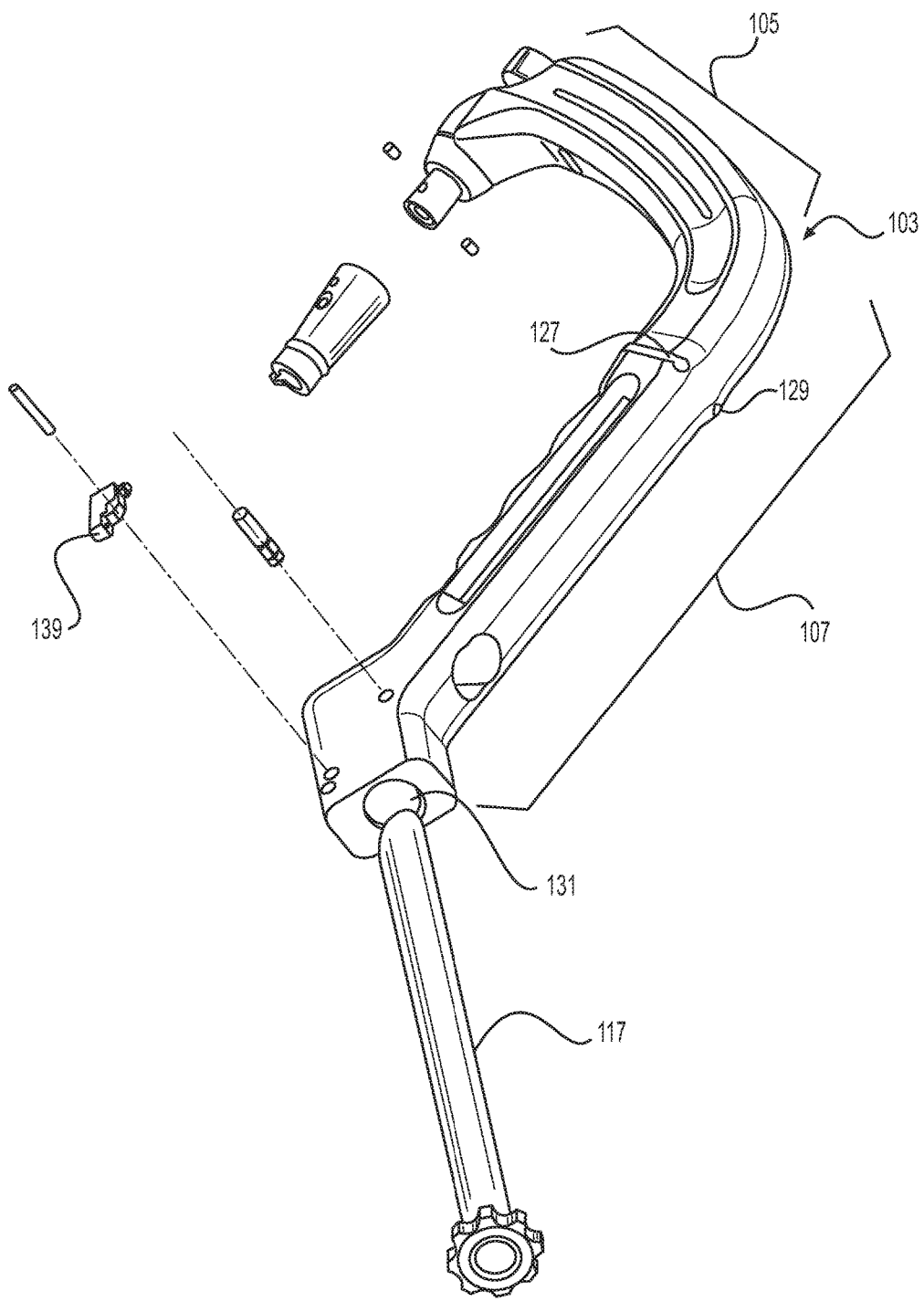
FIGS. 2A-2C illustrate various views of an insertion handle of the system shown in FIGS. 1A and 1B.
Figure 2B:
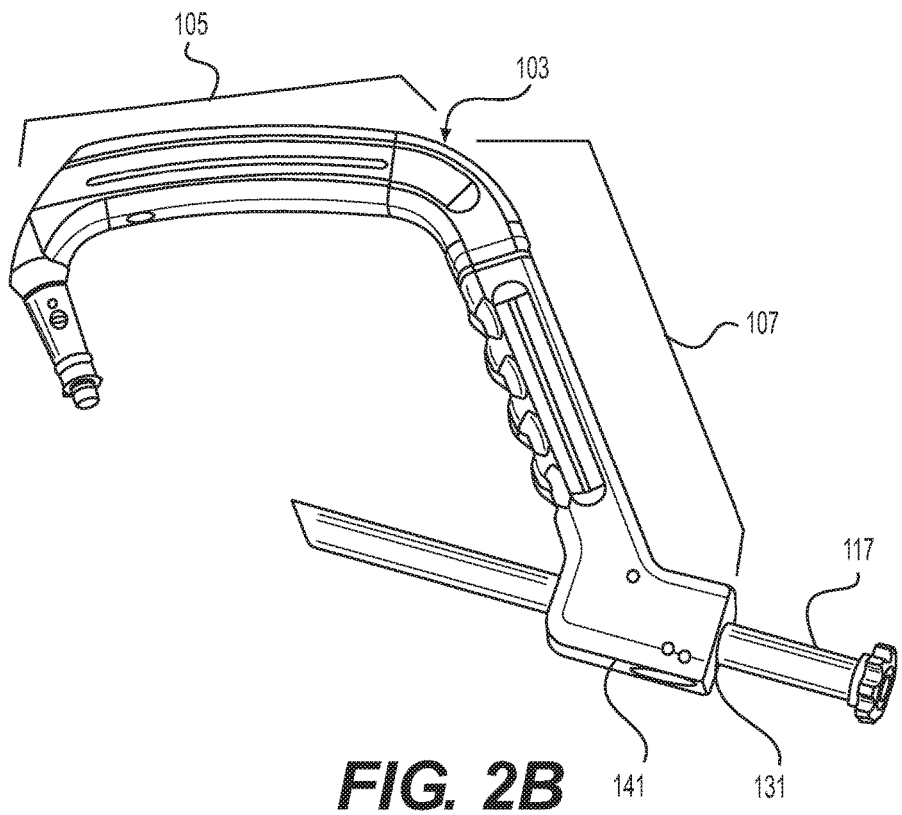
Figure 2C:
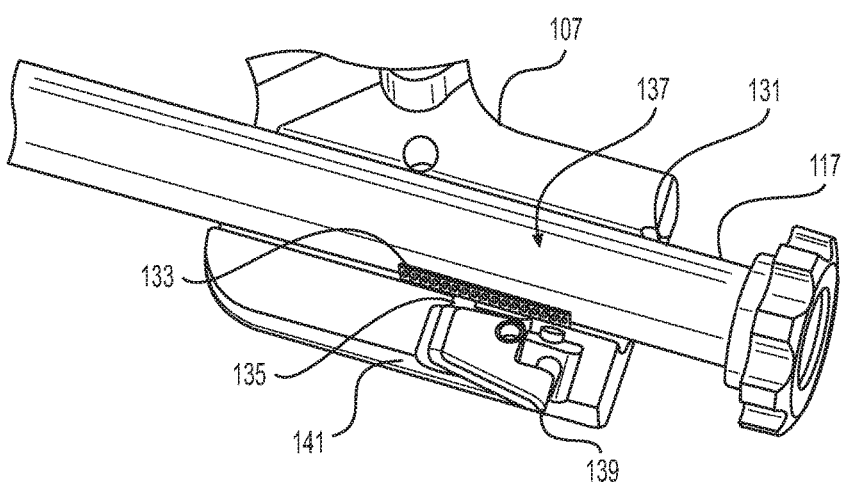

FIGS. 2A-2C illustrate various views of the insertion tool 103 of the system 101 shown in FIGS. 1A and 1B. In particular, FIG. 2A is a partially exploded perspective view of the insertion tool 103 adjacent to the guide sheath 117, FIG. 2B is a perspective view of the insertion tool 103 with the guide sheath 117 partially inserted therein, and FIG. 2C is an enlarged partial cross-sectional view of the engagement between the guide sheath 117 and the insertion tool 103.

The guide sheath 117 can be removably inserted through a guide sheath receiving feature such as a hole 131 formed in the handle portion 107 of the insertion tool 103. The guide sheath hole 131 defines an axis that intersects with a first aperture 123 in the nail 109. The guide sheath 117 can be positioned through the guide sheath hole 131 such that it substantially aligns with the first aperture 123 in the nail 109, which is configured to receive fixation device 119 aimed at the calcar region of the bone. The guide sheath 117 can include a first retention member 133 on an outer surface of the guide sheath 117. The first retention member 133 can include, for example, ridged teeth, protrusions, or other such surface configured to engage with a corresponding second retention member 135 disposed within the guide sheath hole 131. The second retention member 135 can likewise include one or more ridges or protrusions. Together the first and second retention members 133, 135 form a retention mechanism 137 that allows the guide sheath 117 to be ratcheted towards the intramedullary nail 109 while restricting movement of the guide sheath 117 away from the intramedullary nail. The retention release mechanism 139 can disengage the second retention member 135 from the first retention member 133 when pressed by a user. For example, the retention release mechanism 139 can be a button disposed on a lower surface 141 of the handle portion 107. Positioning this retention release mechanism 139 on the lower surface 141 of the insertion handle may prevent a user from accidentally releasing the guide sheath 117 while operating the device (e.g., while grasping the handle portion 107).

FIGS. 3A-3F illustrate one method of steps of implanting an intramedullary nail into a fractured femur 143. Referring first to FIG. 3A, a proximal end of the femur 143 can be accessed and the medullary cavity of the femur 143 can be reamed using a bone drill and reamer 145. Next, as shown in FIG. 3B, the intramedullary nail 109 is coupled to the insertion tool 103 and the intramedullary nail 109 is disposed within the reamed cavity of the femur 143. In FIG. 3C, when used, one or more of the first and second guide wires 113 and 115 may be inserted through the soft tissue, for example, along parallel trajectories on opposing sides of the nail 109. The guide wires 113, 115 can limit or prevent inadvertent rotation of distal fragments of the femur 143 after the nail 109 is in position. The proximal fixation device 119 (e.g., a lag screw or other suitable bone anchor) is also passed through the first aperture 123 in the nail 109 and into the head/neck region of the femur 143. In FIG. 3D, the guide wires 113, 115 are retracted and in FIG. 3E, the distal fixation device 147 can additionally be inserted through the distal aperture 125 in the nail 109. The distal device 147 can be positioned using the guide sheath 117, which is positioned through another opening in the handle portion 107, such that the sheath 1117 is aligned with the distal opening 125 in the nail 109. In FIG. 3F, the insertion tool 103 is disengaged from the nail 109, which is now secured in place via the proximal fixation device 119 and the distal fixation device 147. As shown, the nail 109 may extend along a portion of the length of femur 143. It is also contemplated, however, that the nail 109 may be of different sizes and shapes, for example, of longer lengths and/or different diameters to accommodate different anatomies and fractures.

Interlocking Fixation Devices for Intramedullary Nail Fixation

FIGS. 4A-4D illustrate another embodiment of an intramedullary nail 201, similar to intramedullary nail 109, with the addition of a cross-locking feature for proximal locking of the nail 201. Intramedullary nail 201 may include any of the features described above with respect to intramedullary nail 109. Intramedullary nail 201 may further include two interlocking proximal fixation devices 203, 205 (e.g., bone anchors, fasteners, or screws), for example, by providing converging and diverging purchase, along with bony fixation in the calcar of the femur 229, which is the strongest portion of the hip bone. Accordingly, the risk of failure due to cutout and/or rotation may be reduced.

FIGS. 4A-4D show side, side cross-sectional, and two perspective views, respectively, of the intramedullary nail 201 adjacent to a first fixation device 203. FIGS. 5A-5D illustrate side, side cross-sectional, and two perspective views, respectively, of the first, proximal fixation device 203 inserted through the intramedullary nail 201. FIGS. 6A-6D illustrate side, side cross-sectional, and two perspective views, respectively, of the system with a second, cross-locking fixation device 205 adjacent to the intramedullary nail 201 with the first fixation device 203 inserted therein. FIGS. 7A-7D illustrate side, side cross-sectional, and two perspective views, respectively, of the system with the second fixation device 205 inserted through both the intramedullary nail 201 and the first fixation device 203, thereby creating a cross-locking feature for proximal locking of the nail 201.

Referring to FIGS. 4A-8C together, the intramedullary nail 201 is configured to receive both the first and second fixation devices 203 and 205 therein. The intramedullary nail 201 includes an elongated body 207 having first and second apertures 209 and 211 formed therethrough in a proximal region 213, as well as a third aperture 215 formed in a distal region 217. The first aperture 209 can be sized and configured to receive the first fixation device 203 therethrough and the second aperture 211 can be sized and configured to receive the second fixation device 205 therethrough.

The first fixation device 203, may be the same or similar to the proximal fixation device 119, described herein, and may include a bone screw or anchor configured for proximal locking of the nail 201. For example, the first fixation device 203 may be a calcar screw or anchor configured to be aimed at a calcar region of the proximal humerus. The calcar screw 203 may have a threaded portion at its distal tip and a non-threaded portion along a substantial length of the screw 203. The calcar screw 203 may include traditional polyaxial or fixed angle calcar screws and anchors known in the art.

The second fixation device 205 may also include a bone screw or anchor configured for proximal locking of the nail 201. This bone anchor or screw 205 may be substantially smaller in length and diameter relative to the calcar screw 203. The bone anchor or screw 205 is substantially sized and configured to be positioned through second opening 211 in the proximal end of the nail 201 and into a channel 219 in the first fixation device 203. Thus, the second device 205 is configured to interlock with the first fixation device 203, for example, enhanced purchase and bony fixation to the bone. Although shown with the second fixation device 205 positioned above the first fixation device 203 and angled downwardly into contact with the first fixation device 203, it is also envisioned that these relative positions may be reversed or the fixation devices 203, 205 may otherwise be angled with respect to one another in order to interlock the devices 203, 205 with one another. The second fixation device 205 may be configured to pass through a slot or channel 219 formed in the first fixation device 203. This interlocking feature of the first and second fixation devices 203, 205 can prevent cutout and rotation by providing converging and diverging purchase. In the case of a femur, this can also provide bony fixation in the calcar. The elongated slot 219 in the first fixation device 203 allows for controlled collapse, which leverages the natural compression between fragments from weight bearing or ligamentotaxis. Limited collapse is controlled by the length of the slot 219 to prevent the uncontrolled and excessive shortening of the femoral neck. The first fixation device 203 may include distal threads 221 and a proximal drive interface 223 configured to engage with a driver (not shown). The second fixation device 205 may have a narrower diameter than the first fixation device 203 such that the second fixation device 205 can pass through the slot 219 in the first fixation device 203. The second fixation device 205 may also include distal threads 225 and a proximal drive interface 227 configured to engage with a driver (not shown).

The slot 219 can be disposed in the mid-shaft of the first fixation device 203 and may be sized and configured to allow the second fixation device 205 to pass therethrough. The slot 219 may be longer than necessary to allow translation of the first fixation device 203 after the second fixation device 205 is in place. The slot 219 may be strong enough to prevent rotation of the first fixation device 203 after the second fixation device 205 is in position. The slot 219 may have beveled proximal and distal edges to maximize material in the first fixation device 203 while allowing proximal and distal clearance of the second fixation device 205. The slot 219, in the first fixation device 203, may be symmetric to allow positioning of the second fixation device 205 in 180° increments, for example.

Figure 7B:
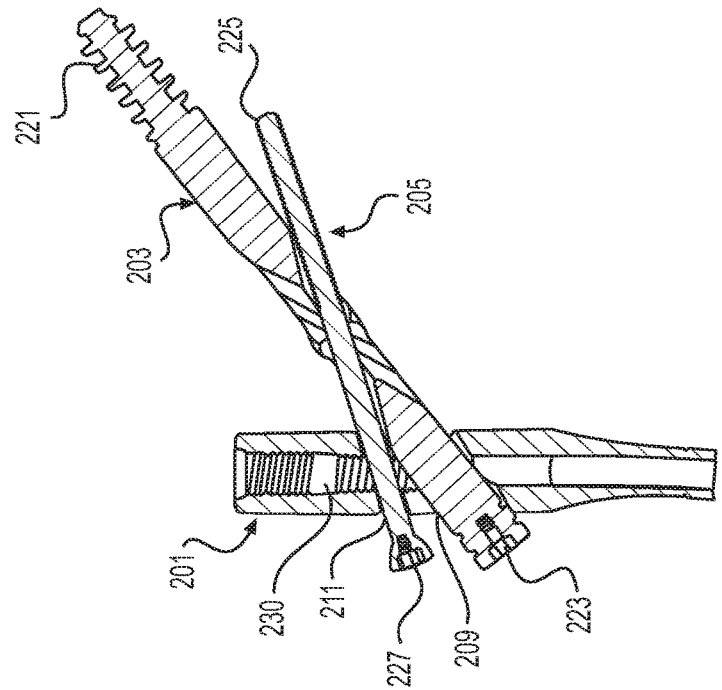
Figure 7A:
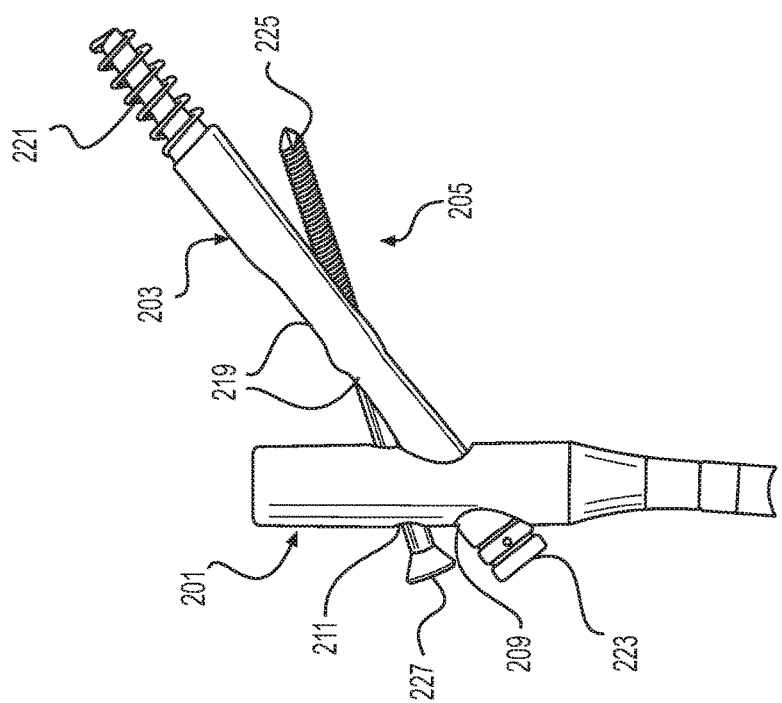

In at least one embodiment, a locking device 230, such as a set screw or washer, may be used to lock the first and/or the second fixation devices 203, 205 into position. As best seen in FIG. 7B, the locking device 230 may be threaded through a hollow interior portion of the nail 201. The locking device 230 may have external threads, which are sized and configured to correspond to mating internal threads along the hollow interior portion of the nail 201. As the locking device 230 is threaded downwardly and comes into contact with the first or second fixation devices 203, 205, the respective fixation device 203, 205 is locked into position relative to the nail 201. In some embodiments, the interlocking fixation devices 203, 205 can be used selectively. For example, the threaded locking device 230 may be threaded to engage the second fixation device 205; alternatively, the threaded locking device 230 may be threaded further down to lock the first fixation device 203, for example, if the second fixation device 205 is not used. This allows users the choice of a traditional or interlocking construct intraoperatively.

An insertion tool 103 for implanting the system including the nail 201 and the interlocking first and second fixation devices 203 and 205 can be substantially similar to the system 101 described above with respect to FIGS. 1A-2C, except that an additional guide sheath hole may be formed in the handle portion 107 to accommodate a guide sheath along an appropriate trajectory to insert the second fixation device 205 through the second aperture 211 in the nail 201 and into engagement with the first fixation device 203.

FIGS. 8A-8C illustrate one method of steps of implanting an intramedullary nail 201 with interlocking fixation devices 203, 205 into a fractured femur 229. Referring first to FIG. 8A, the nail 201 has been inserted into a reamed medullary cavity of the femur 229 and the first fixation device 203 has been inserted through the first aperture 209 in the nail 201, similar to the technique described above with respect to FIGS. 3A-3D. Referring to FIG. 8B, a distal fixation device 231 can be inserted through the third aperture 215 in the nail 201, similar to the technique described above with respect to FIG. 3E. Referring to FIG. 8C, the second fixation device 205 is inserted through the second aperture 211 in the nail 201 and through the slot 219 in the first fixation device 203. As noted, these intersecting first and second fixation devices 203, 205 provide additional purchase in the head and neck region of the femur 229, and in particular the second fixation device 205 can provide bony fixation in the calcar. Accordingly, the interlocking first and second fixation devices 203, 205 can provide for improved stability and protection against common modes of intramedullary nail implant failure.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for inserting an intramedullary nail into a bone, the system comprising:
    an intramedullary nail having a proximal end, a distal end, at least one side surface extending between the proximal end and the distal end, and an aperture through the intramedullary nail; and
    an insertion tool comprising:
        a handle portion having a guide sheath portion having a lower surface;
        a coupling portion extending from the handle portion, the coupling portion configured to removably couple to the proximal end of the intramedullary nail;
        a guide sheath hole having a longitudinal axis formed in the guide sheath portion of the handle portion, the longitudinal axis being parallel to the lower surface of the guide sheath portion, and the guide sheath hole configured to receive a guide sheath therethrough, the guide sheath hole positioned such that, when the intramedullary nail is coupled to the coupling portion, the guide sheath hole substantially aligns with the aperture in the intramedullary nail; and
        a retention mechanism comprising:
            a first retention member positioned along the guide sheath hole and configured to pivotably engage with a second retention member on the guide sheath to restrict movement of the guide sheath with respect to the guide sheath hole; and
            a retention release mechanism disposed on the lower surface of the guide sheath portion of the handle portion; wherein the retention mechanism allows movement of the guide sheath in a first direction and restricts movement of the guide sheath in a second direction, wherein the retention mechanism including the first retention member and the retention release mechanism have a unitary body pivotable about a pivot point located between the guide sheath hole and the lower surface of the guide sheath portion of the handle portion.

2. The system of claim 1, further comprising a guide wire hole configured to receive a guide wire therethrough, wherein the guide wire hole is a first guide wire hole spaced apart from the guide sheath hole and positioned such that, when the intramedullary nail is coupled to the coupling portion, the guide wire hole defines an axis that runs adjacent to the side surface of the intramedullary nail, and the system further comprising a second guide wire hole disposed at a position spaced apart from the first guide wire hole, wherein the axes of the first and second guide wire holes are substantially parallel.

3. The system of claim 1, further comprising the guide sheath, wherein the guide sheath comprises a lumen configured to receive a fixation device therethrough, and wherein the second retention member is disposed on an outer surface of the guide sheath.

4. The system of claim 1, wherein the handle portion is configured to engage with the coupling portion at a first end of the handle portion, and wherein the retention release mechanism comprises a release button disposed on a second, opposite end of the handle portion.

5. The system of claim 1, wherein the first and second retention members comprise corresponding ridges that, when engaged with one another, permit ratcheted movement in one direction only.

6. The system of claim 1, wherein the aperture in the intramedullary nail is a first aperture, the intramedullary nail comprising a second aperture spaced apart from the first aperture, wherein the system further comprises:
 a first fixation device configured to pass through the first aperture; and
 a second fixation device configured to pass through the second aperture such that the second fixation device intersects with the first fixation device.

7. The system of claim 6, wherein the first fixation device comprises a slot, and wherein the second fixation device is configured to pass at least partially through the slot.

8. The system of claim 2, wherein when first and second guide wires are received in the first and second guide wire holes, respectively, the first and second guide wires extend on opposite sides of the intramedullary nail.

9. The system of claim 1, wherein the guide sheath is a tube having an outer surface, and the second retention member is on the outer surface of the guide sheath.

10. The system of claim 1, wherein the handle portion defines a second guide sheath hole, and when the guide sheath is positioned through the second guide sheath hole, the guide sheath is aligned with a distal opening in the intramedullary nail.

11. The system of claim 10, wherein the second guide sheath hole does not include a retention mechanism.

12. A method for inserting an intramedullary nail into a patient, the method comprising:
 disposing a nail into a medullary canal of a patient along a first axis, the nail coupled at its proximal end to a coupling portion of an insertion tool, the insertion tool including a handle portion extending away from the coupling portion, the handle portion having a guide sheath portion having a lower surface;
 passing a guide wire through a guide wire hole in the handle portion of the insertion tool along a second axis transverse to the first axis such that the guide wire runs adjacent to a side surface of the nail;
 inserting a guide sheath into a guide sheath hole having a longitudinal axis in the guide sheath portion of the handle portion, the longitudinal axis being parallel to the lower surface of the guide sheath portion, the guide sheath being retained in the guide sheath portion of the handle portion with a retention mechanism, wherein the retention mechanism includes a first retention member and a retention release mechanism have a unitary body pivotable about a pivot point located between the guide sheath hole and the lower surface of the guide sheath portion of the handle portion, the retention mechanism allows movement of the guide sheath in a first direction and restricts movement of the guide sheath in a second direction, and
 inserting a fixation device through the guide sheath in the handle portion such that the fixation device passes through an aperture formed in the nail; and
 releasing the retention mechanism with the retention release mechanism disposed on the lower surface of the guide sheath portion of the handle portion.

13. The method of claim 12, wherein inserting the fixation device comprises:
 inserting the guide sheath through the guide sheath hole such that the first retention member in the guide sheath hole engages with a second retention member on an outer surface of the guide sheath; and
 inserting the fixation device through the guide sheath.

14. The method of claim 13, wherein the first and second retention members comprise corresponding ridges that, when engaged with one another, permit ratcheted movement in one direction only.

15. The method of claim 13, further comprising disengaging the first and second retention members by actuating the release mechanism disposed on the handle portion.

16. The method of claim 12, further comprising passing a second guide wire through a second guide wire hole in the handle portion of the insertion tool along a third axis substantially parallel to the second axis.

17. The method of claim 12, wherein the fixation device is a first fixation device, the method further comprising inserting a second fixation device through a second aperture formed in the nail such that the second fixation device intersects the first fixation device.

18. The method of claim 17, further comprising inserting a third fixation device through a third aperture formed in a distal portion of the nail.

* * * * *